(12) United States Patent
Peterson et al.

(10) Patent No.: US 6,862,951 B2
(45) Date of Patent: Mar. 8, 2005

(54) FOOTSWITCH

(75) Inventors: Robert H. Peterson, Rancho Santa Margarita, CA (US); David Thoe, Aliso Viejo, CA (US); Jiansheng Zhou, Cerritos, CA (US); Dac Vu, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 48 days.

(21) Appl. No.: 10/271,505

(22) Filed: Oct. 16, 2002

(65) Prior Publication Data

US 2004/0035242 A1 Feb. 26, 2004

Related U.S. Application Data

(63) Continuation-in-part of application No. 29/166,339, filed on Aug. 26, 2002, now Pat. No. Des. 478,323.
(60) Provisional application No. 60/408,211, filed on Sep. 14, 2002.

(51) Int. Cl.[7] .................................................. G05G 1/14
(52) U.S. Cl. ........................................... 74/560; 74/512
(58) Field of Search ........................... 200/86.5; 74/560, 74/561, 512

(56) References Cited

U.S. PATENT DOCUMENTS

| 4,267,414 A | | 5/1981 | Brueggeman | |
| 4,383,167 A | * | 5/1983 | Gmeinder et al. | 74/512 |
| 4,837,857 A | | 6/1989 | Scheller et al. | |
| 4,901,454 A | | 2/1990 | Walkhoff | |
| 4,965,417 A | | 10/1990 | Massie | |
| 4,983,901 A | | 1/1991 | Lehmer | |
| 5,091,656 A | | 2/1992 | Gahn | |
| 5,268,624 A | | 12/1993 | Zanger | |
| 5,554,894 A | | 9/1996 | Sepielli | |
| 5,580,347 A | | 12/1996 | Reimels | |
| 5,635,777 A | | 6/1997 | Telymonde et al. | |
| 5,787,760 A | | 8/1998 | Thorlakson | |
| 5,983,749 A | | 11/1999 | Holtorf | |
| 5,990,400 A | * | 11/1999 | Hoshino | 84/422.1 |
| 6,010,496 A | | 1/2000 | Appelbaum et al. | |
| 6,150,623 A | | 11/2000 | Chen | |
| 6,179,829 B1 | | 1/2001 | Bisch et al. | |
| 6,360,630 B2 | * | 3/2002 | Holtorf | 74/512 |
| 6,452,120 B1 | | 9/2002 | Chen | |
| 6,452,123 B1 | | 9/2002 | Chen | |
| 6,674,030 B2 | | 1/2004 | Chen et al. | |
| 2002/0045887 A1 | | 4/2002 | DeHoogh et al. | |
| 2003/0047434 A1 | | 3/2003 | Hanson et al. | |
| 2003/0213333 A1 | * | 11/2003 | McVicar | 74/560 |

FOREIGN PATENT DOCUMENTS

| DE | 39 03 401 A | 8/1990 |
| GB | 1 063 067 A | 3/1967 |
| JP | 2000 229102 | 8/2000 |
| WO | WO 96/13845 | 5/1996 |
| WO | WO 98/08442 | 3/1998 |
| WO | WO 99/14648 | 3/1999 |
| WO | WO 00/12037 | 3/2000 |
| WO | WO 02/01310 | 1/2002 |
| WO | WO 03/053293 A2 | 7/2003 |
| WO | WO 03/053294 A2 | 7/2003 |

* cited by examiner

Primary Examiner—David A. Bucci
Assistant Examiner—Bradley J. Van Pelt
(74) Attorney, Agent, or Firm—Jeffrey S. Schira

(57) ABSTRACT

A footswitch having an adjustable treadle and switch placements, thereby helping to make the footswitch ergonomically more correct for a variety of users.

12 Claims, 13 Drawing Sheets

FOOTSWITCH

This application claims the benefit of U.S. Provisional Patent Application Ser. No. 60/408,211, filed Sep. 4, 2002, and is a continuation in part of U.S. patent application Ser. No. 29/166,339, filed Aug. 26, 2002, now U.S. Pat. No. D.478,323.

BACKGROUND OF THE INVENTION

This invention relates generally to the field of surgical consoles and, more particularly, to footswitches used to control microsurgical consoles.

During modern surgery, particularly ophthalmic surgery, the surgeon uses a variety of pneumatic and electronically driven microsurgical handpieces. The handpieces are operated by a microprocessor-driven surgical console that receives inputs from the surgeon or an assistant by a variety of peripheral devices including footswitches. Prior art footswitches are disclosed in U.S. Pat. No. 4,837,857 (Scheller, et al.), U.S. Pat. No. 4,965,417 (Massie), U.S. Pat. No. 4,983,901 (Lehmer), U.S. Pat. No. 5,091,656 (Gahn), U.S. Pat. No. 5,268,624 (Zanger), U.S. Pat. No. 5,554,894 (Sepielli), U.S. Pat. No. 5,580,347 (Reimels), U.S. Pat. No. 5,635,777 (Telymonde, et al.), U.S. Pat. No. 5,787,760 (Thorlakson), U.S. Pat. No. 5,983,749 (Holtorf) and U.S. Pat. No. 6,179,829 B1 (Bisch, et al.) and International Patent Application Publication Nos. WO 98/08442 (Bisch, et al.), WO 00/12037 (Chen) and WO 02/01310 (Chen), the entire contents of which being incorporated herein by reference. These patents, however, focus primarily on functional attributes of footswitches, not the ergonomics of footswitches.

Accordingly, a need continues to exist for an ergonomically improved footswitch.

BRIEF SUMMARY OF THE INVENTION

The present invention improves upon the prior art surgical footswitches by providing a footswitch having an adjustable treadle and switch placements, thereby helping to make the footswitch ergonomically more correct for a variety of users.

Accordingly, one objective of the present invention is to provide a surgical footswitch that can be adjusted to accommodate different sized feet.

Another objective of the present invention is to provide an ergonomically adjustable surgical footswitch.

Another objective of the present invention is to provide a surgical footswitch having adjustable switches.

These and other advantages and objectives of the present invention will become apparent from the detailed description and claims that follow.

DETAILED DESCRIPTION OF THE INVENTION

Figure 1:
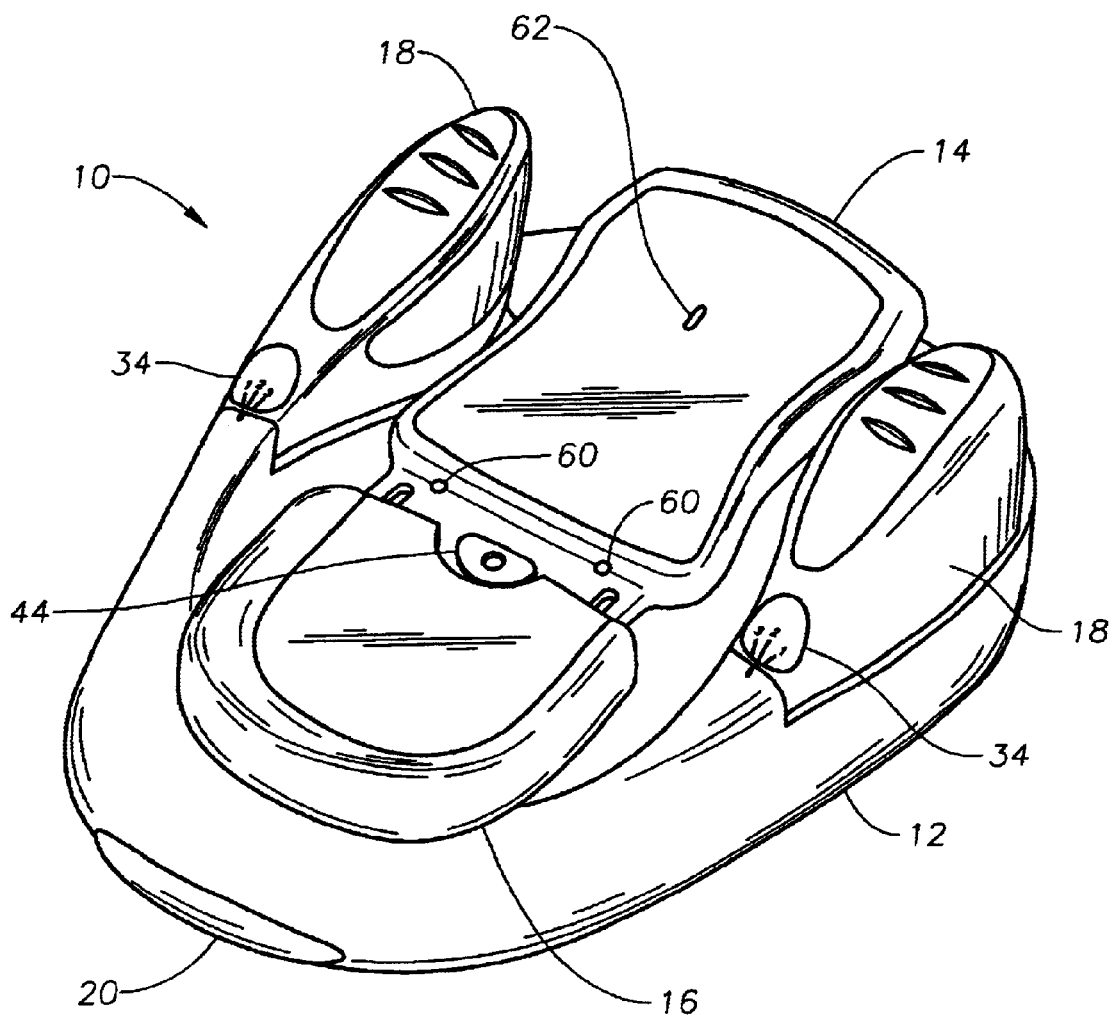
FIG. 1 is a perspective view of the surgical footswitch of the present invention.
Figure 2A:
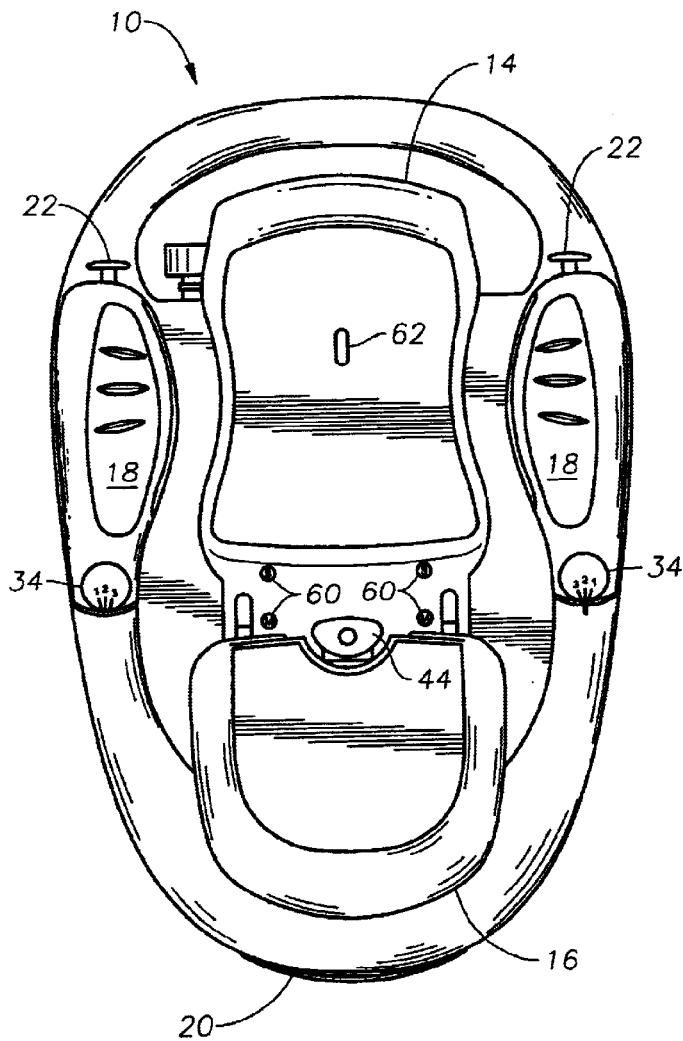
FIGS. 2A–2C are enlarged plan views of the footswitch of the present invention illustrating the adjustability of the side switches.
Figure 2B:
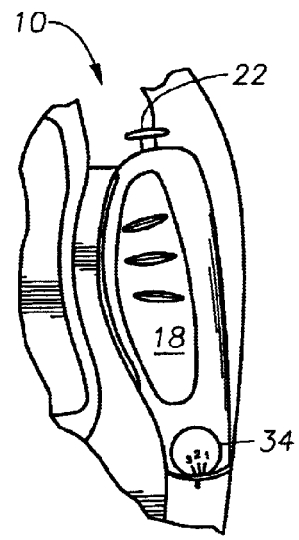
Figure 2C:
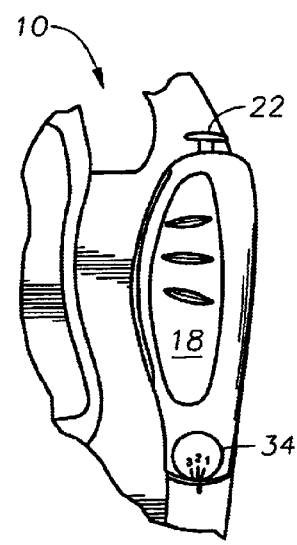
Figure 3:
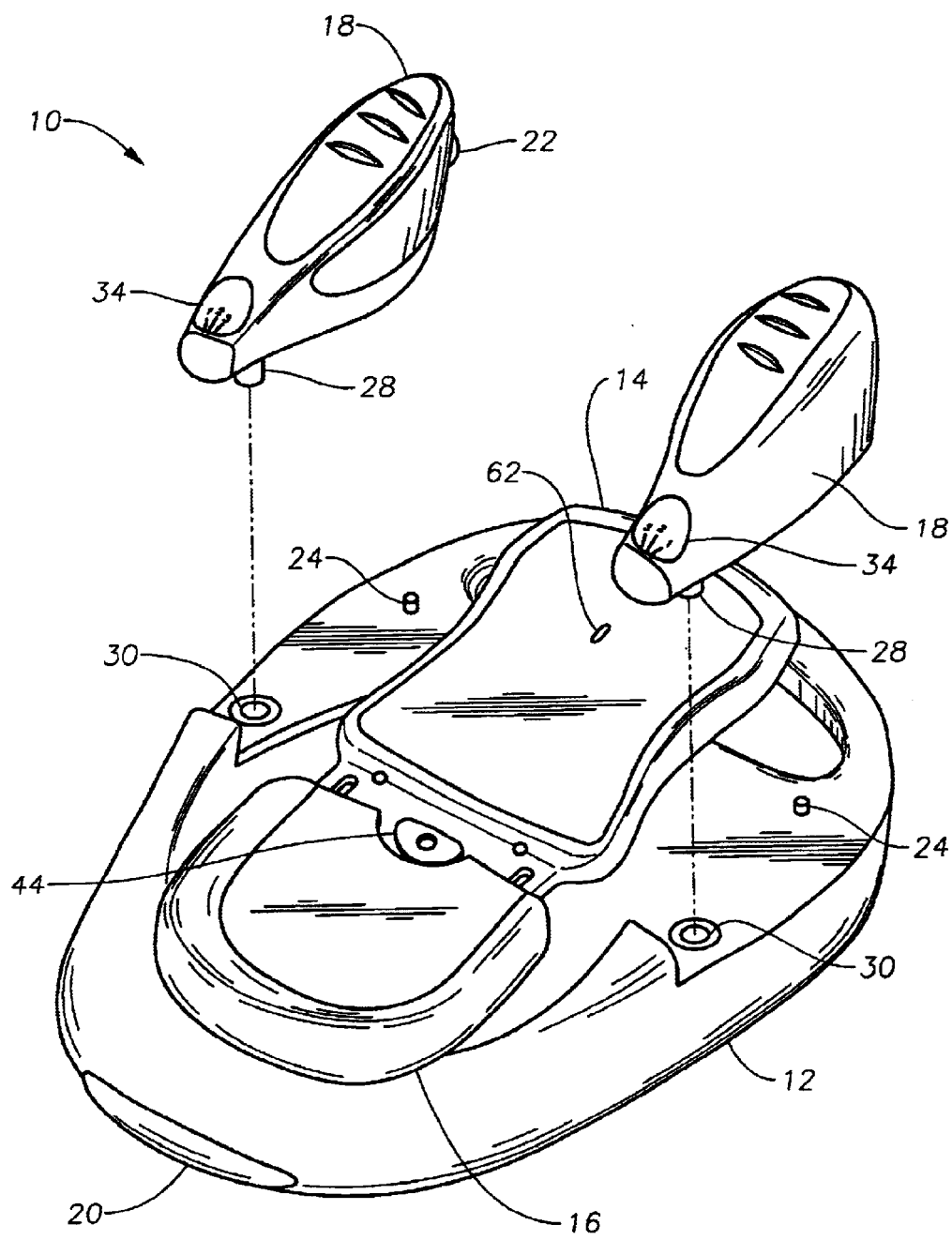
FIG. 3 is an exploded perspective view of the surgical footswitch illustrating the assembly of the side switches.
Figure 4A:
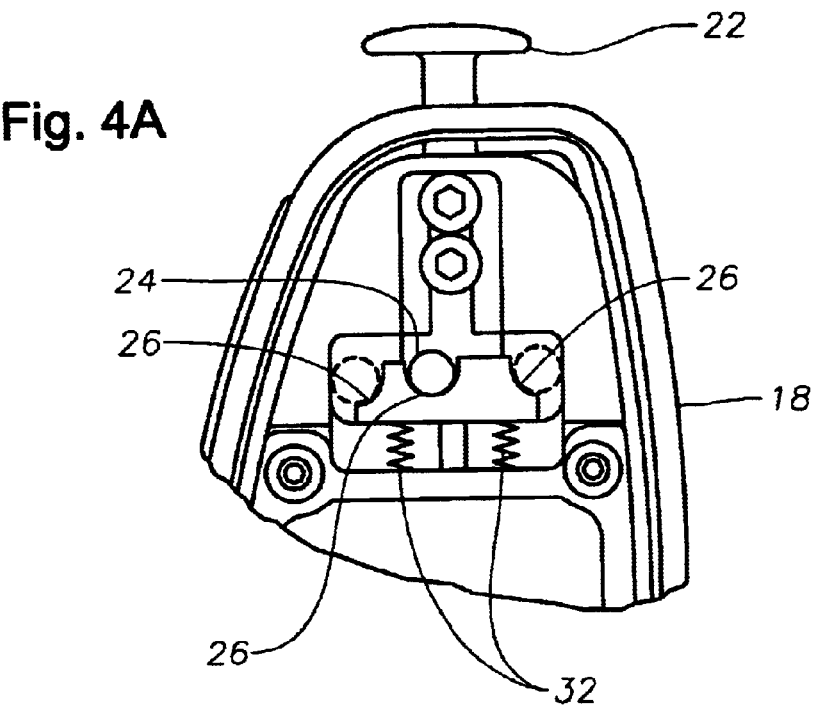
FIGS. 4A–4B are bottom plan views of the side switches that may be used with the footswitch of the present invention illustrating the operation of the rotational locking mechanism.
Figure 4B:
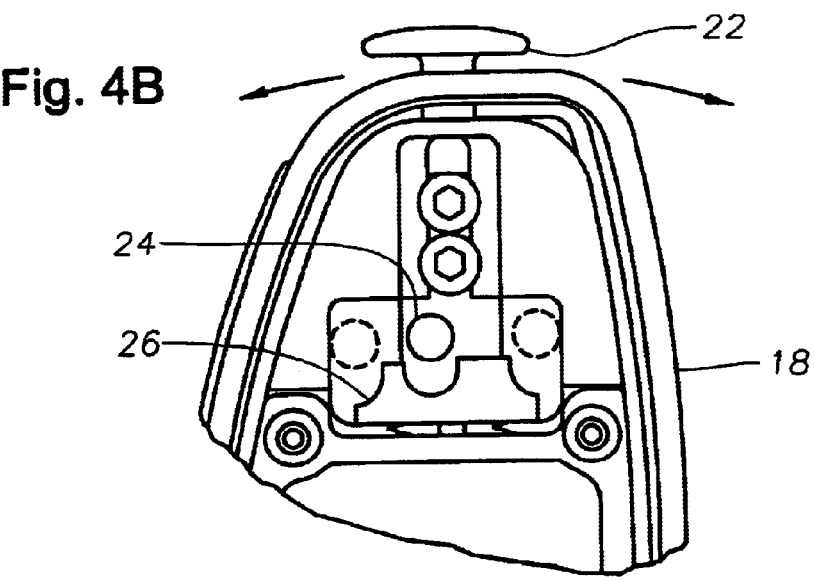
Figure 5:
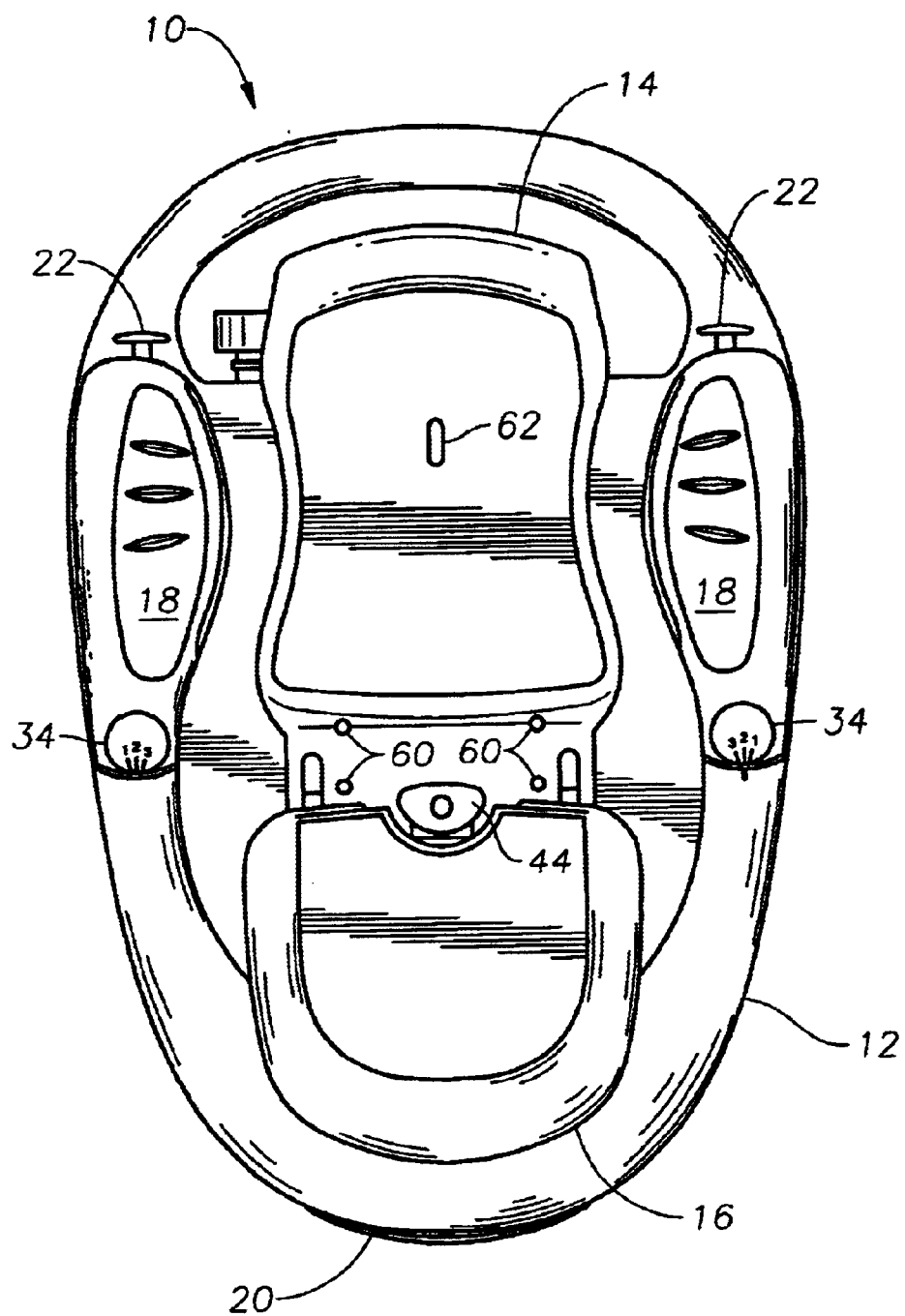
FIG. 5 is a top plan view of the footswitch of the present invention.

As best seen in FIG. 1, footswitch 10 of the present invention generally includes base 12, treadle 14 having heel cup 16 and side or wing switches 18, all of which can be made from any suitable material, such as stainless steel, titanium or plastic. Base 12 may contain protective bumper 20 made from a relatively soft elastomeric material. As best seen in FIGS. 2A–2C, 3 and 4A–4B, side switches 18 may be adjusted inwardly (FIG. 2B) or outwardly (FIG. 2C) to increase or decrease the distance between switches 18 and accommodate for variations in the width of user foot 100. Such adjustment is accomplished by pushing on locking buttons 22, causing locking pin 24 on base 12 to be released from within detents 26 in switches 18 and rotating about pins 28 in holes 30 located on base 12. When buttons 22 are released, springs 32 push detents 26 against locking pin 24, thereby holding switches 18 in a locked position. The relative position of switches 18 may be determined visually by the use of switch position indicators 34, as best seen in FIGS. 2B and 2C.

Figure 6:
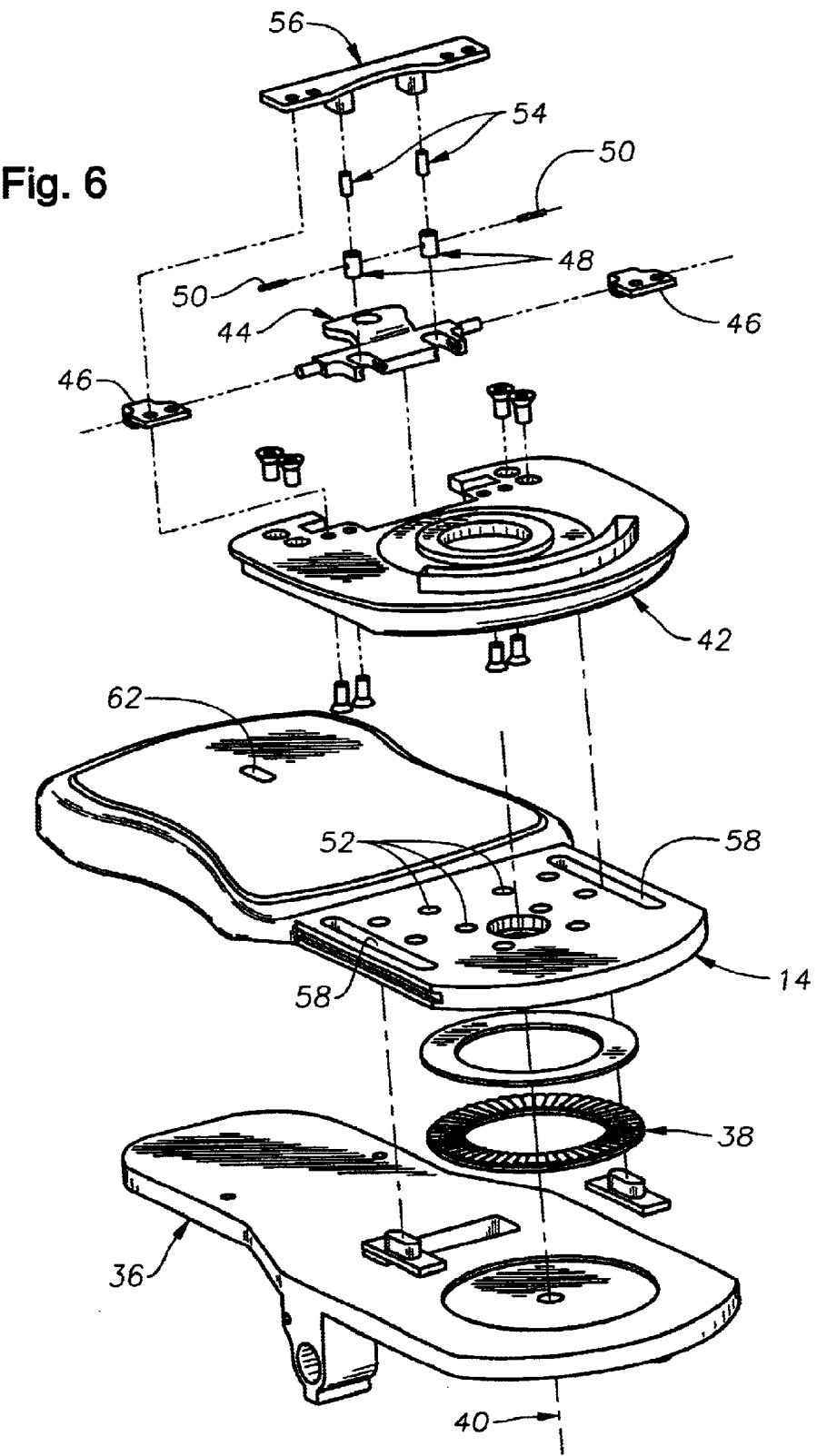
FIG. 6 is an exploded assembly drawing of the heel cup slide adjustment mechanism that may be used with the footswitch of the present invention.
Figure 7A:
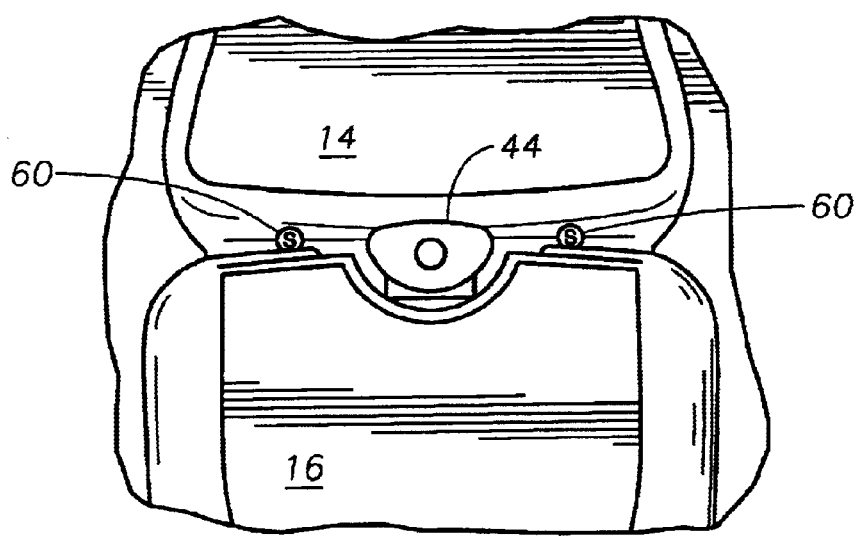
FIGS. 7A–7B are top plan views of the heel cup that may be used with the footswitch of the present invention illustrating the operation of the slidable heel cup adjustment mechanism.
Figure 7B:
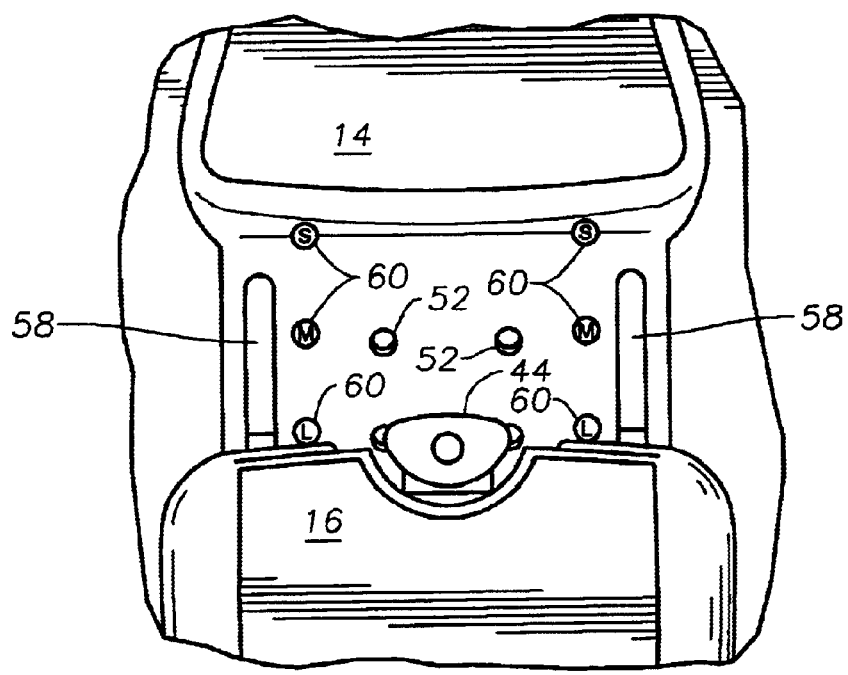

As best seen in FIGS. 5, 6 and 7A–7B, the length of treadle 14 may be adjusted by sliding movement of heel cup 16. As best seen in FIG. 6, treadle 14 is mounted to treadle base 36 by thrust bearing 38, thereby allowing treadle 14 to pivot about axis 40. Heel cup slide 42 is received on treadle 14 and contains locking lever 44, which is held onto heel cup slide 42 by retainers 46. Locking pins 48 are held within locking lever 44 by shafts 50. Locking pins 48 are biased into locking pin holes 52 in treadle 14 by springs 54 pushing against locking pin retainer 56. In this manner, pushing on locking lever 44 pulls locking pins 48 out of locking pin holes 52 and allows heel cup slide 42 to slide lengthwise along slots 58 in treadle 14 as illustrated in FIGS. 7A–7B. The relative position of heel cup 16 relative to treadle 14 may be visually indicated by indicators 60. In addition, treadle 14 may contain raised reference point 62, indicating the center of treadle 14.

Figure 10:
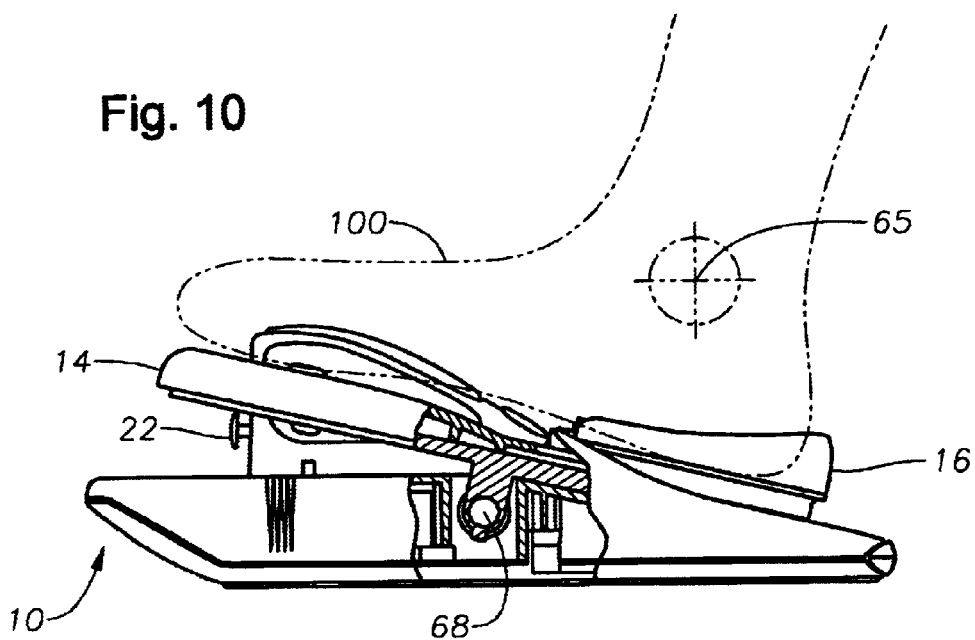
FIG. 10 is a side partial cross-sectional view of the footswitch of the present invention illustrating the location of the treadle pivot point with respect to the ankle of the user.

The width and length adjustments described above preferably allow footswitch 10 to be adjusted to accommodate the $5^{th}$ percentile female to the $95^{th}$ percentile male foot width and length, with or without shoes. As best seen in FIG. 10, ankle rotation axis 65 of foot 100 is located behind pivot axis 68 of treadle 14 for all three treadle lengths.

Figure 8:
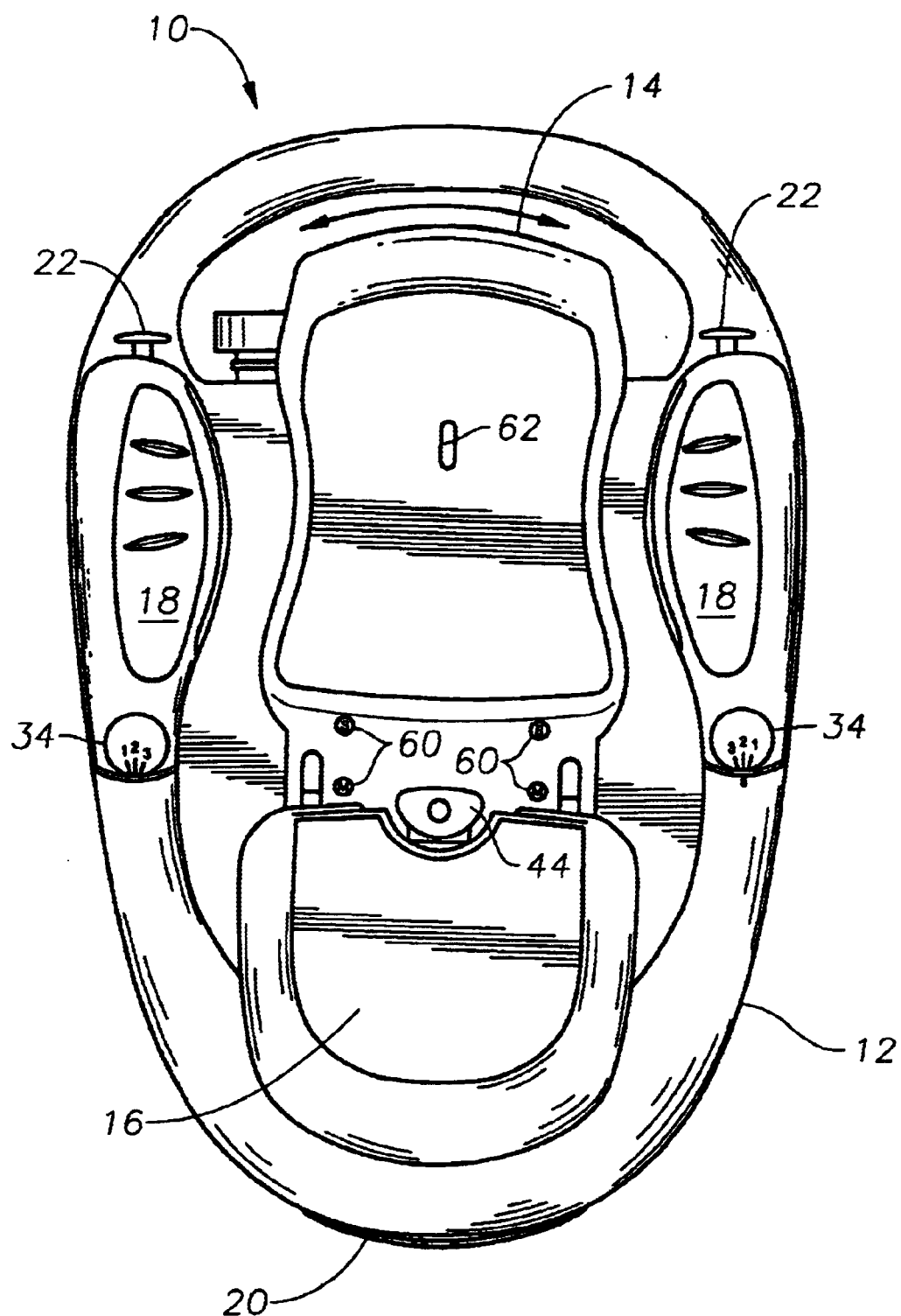
FIG. 8 is a top plan view of the footswitch of the present invention similar to FIG. 6, but illustrating the rotational operation of the treadle.
Figure 9A:
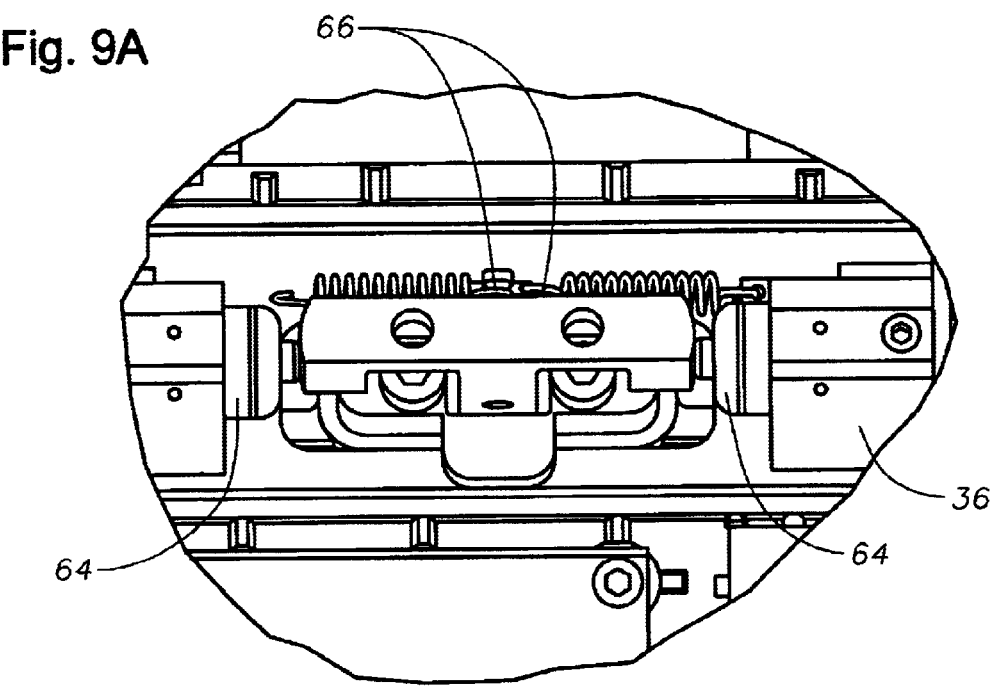
FIGS. 9A–9B are bottom plan views of the treadle switches that may be used with the footswitch of the present invention.
Figure 9B:
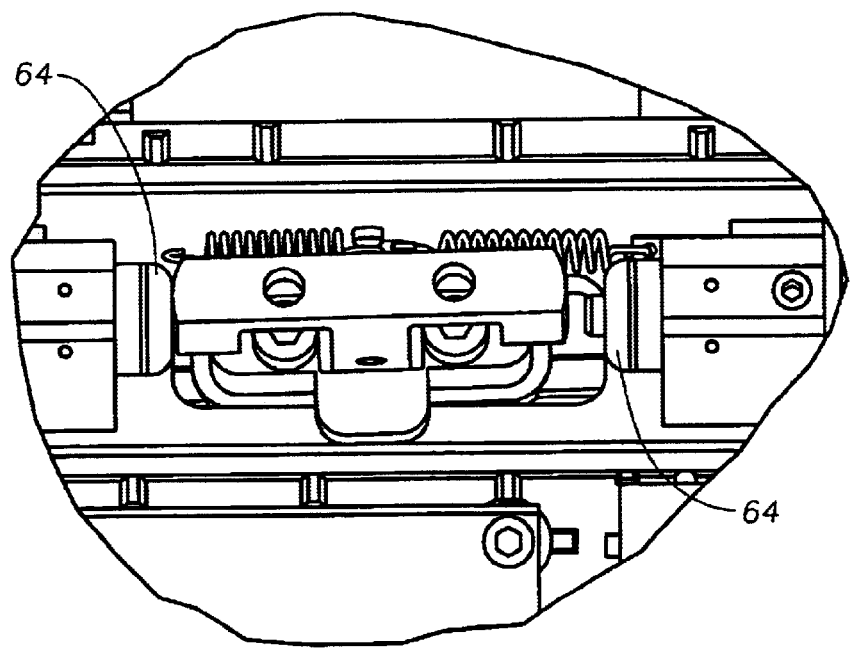
Figure 11A:
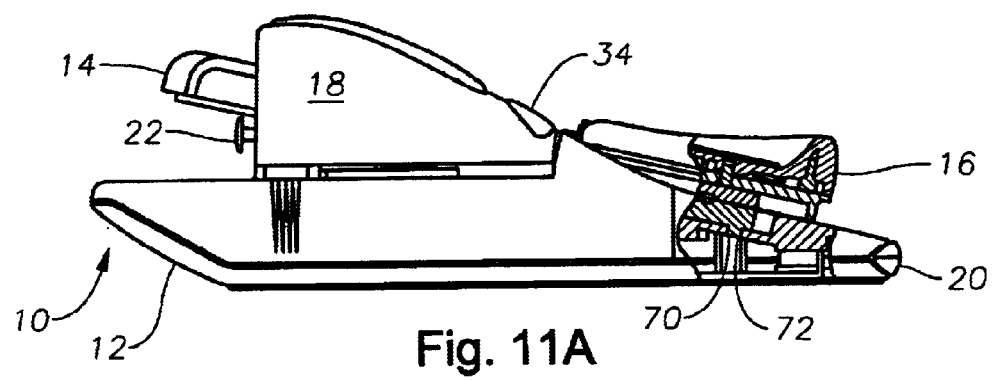
FIGS. 11A–11B are side plan view of the footswitch of the present invention illustrating the operation of the treadle rotation lock.
Figure 11B:
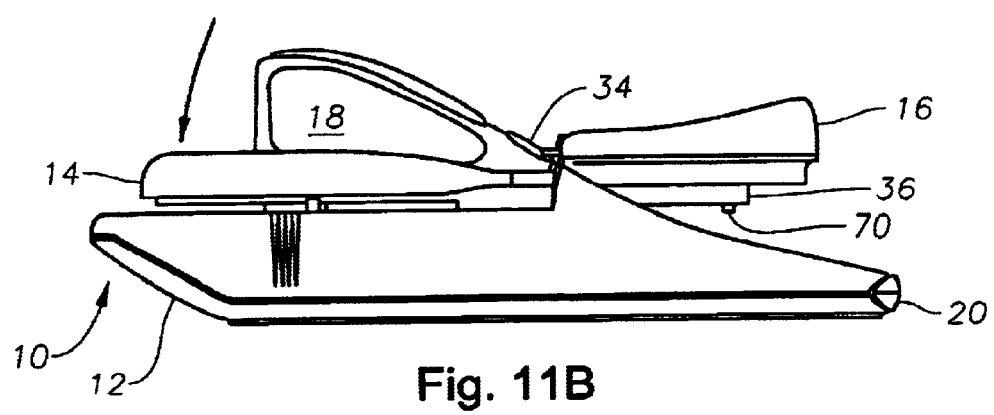
Figure 14:
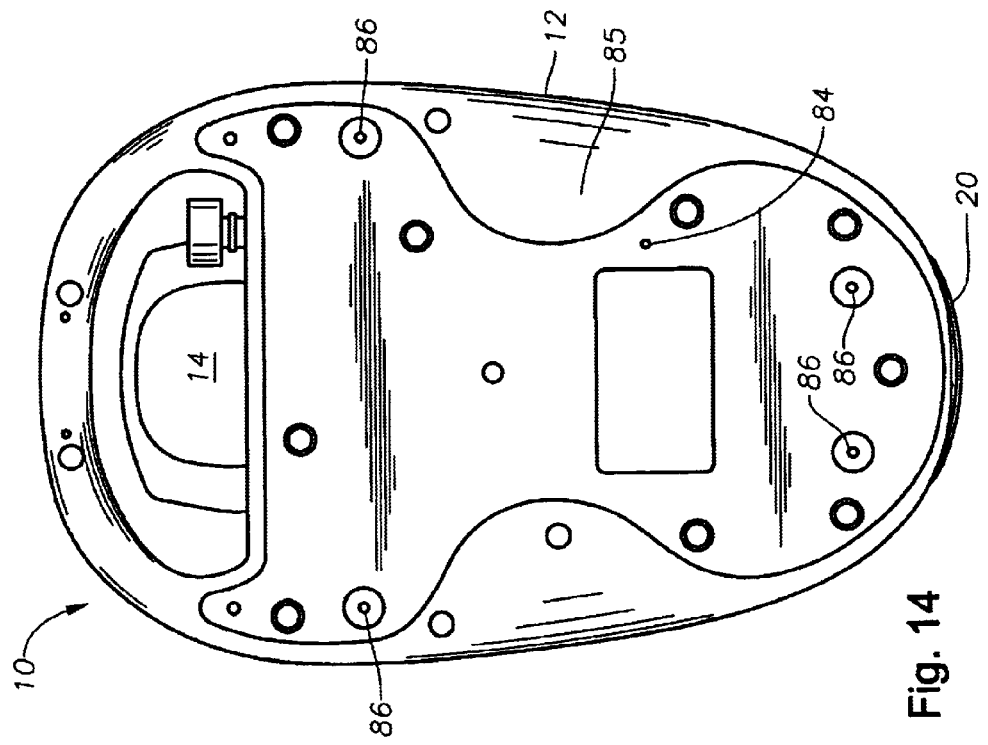
FIG. 14 is a bottom plan view of the footswitch of the present invention.

As best seen in FIGS. 8 and 9A–9B, treadle 14 may rotate or counter-rotate about thrust bearing 38 to operate left and right switches 64, which are mounted on treadle base 36. Return springs 66 provide for automatic centering of treadle 14 following rotation. As best seen in FIGS. 11A and 11B, treadle base 36 contains alignment pin 70 hat fits within hole 72 in base 12 when treadle 14 is in the resting, non-pivoted position. Such a construction prevent rotation of treadle 14 to activation switches 64 when treadle is in the resting, non-pivoted position (FIG. 11A), but allows rotation of treadle 14 when treadle 14 is depressed or pivoted (FIG. 11B).

Figure 12:
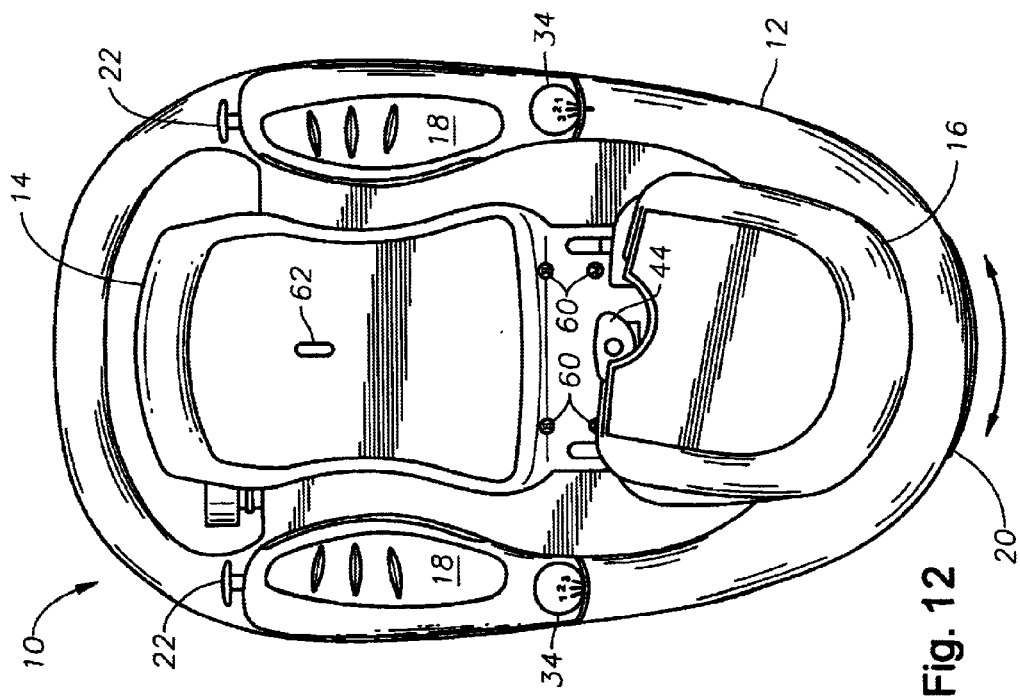
FIG. 12 is a top plan view of the footswitch of the present invention similar to FIGS. 6 and 8, but illustrating the rotational operation of the heel cup.
Figure 13:
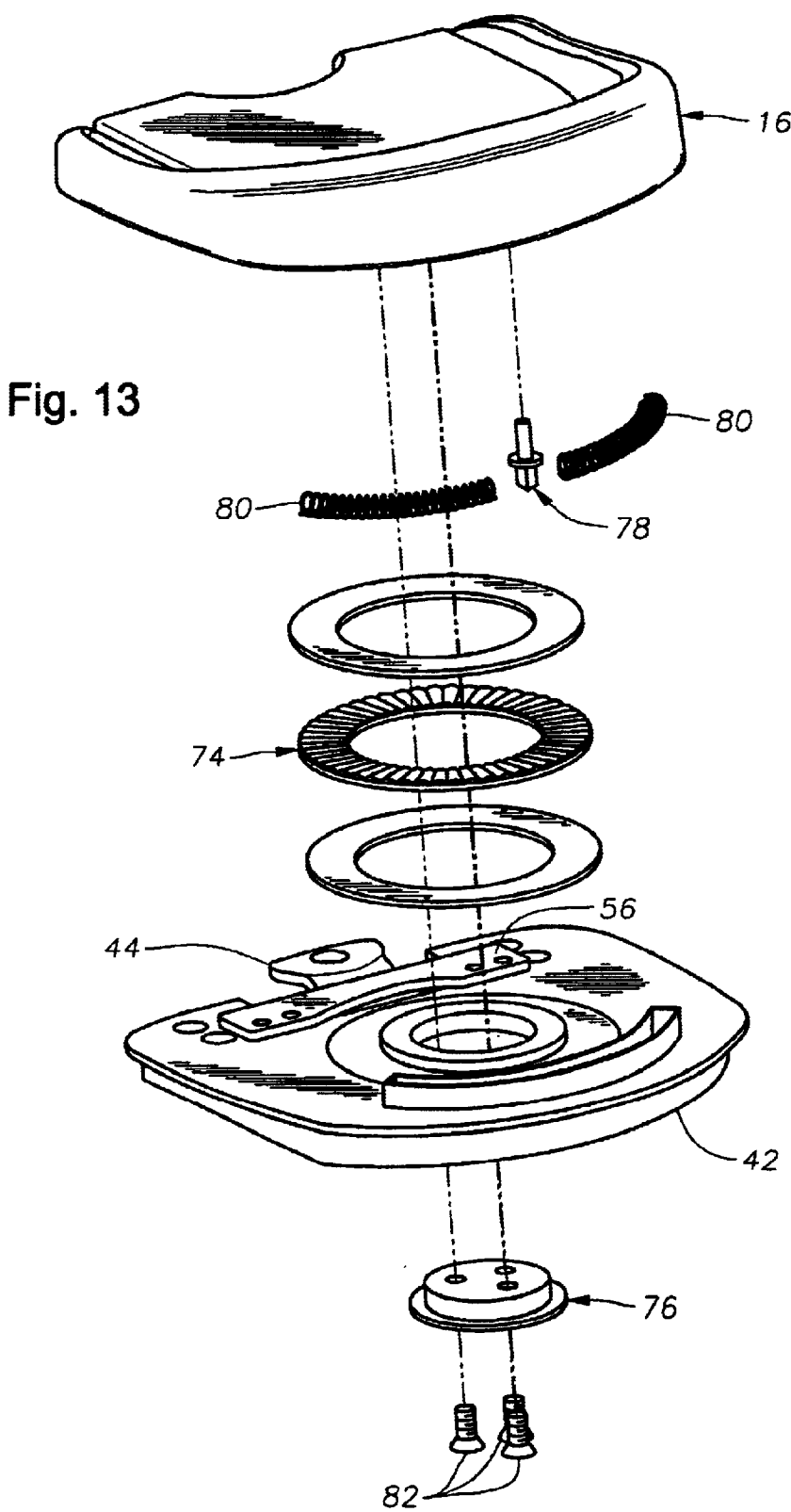
FIG. 13 is an exploded assembly drawing of the heel cup rotation mechanism.

As shown in FIGS. 12 and 13, heel cup 16 is mounted to heel cup slide 42 using thrust bearing 74, alignment cap 76 and screws 82. Such a construction allow for the rotation of heel cup 16 independently of any rotation of treadle 14 (as show in FIGS. 8 and 9A–9B) and allows for the operation of side switches 18 when treadle is in the resting and rotationally locked position (FIG. 11A). Return lever, 78, mounted to heel cup 16 acts against return springs 80 to provide for automatic centering of heel cup 16 in the resting position.

Figure 15A:
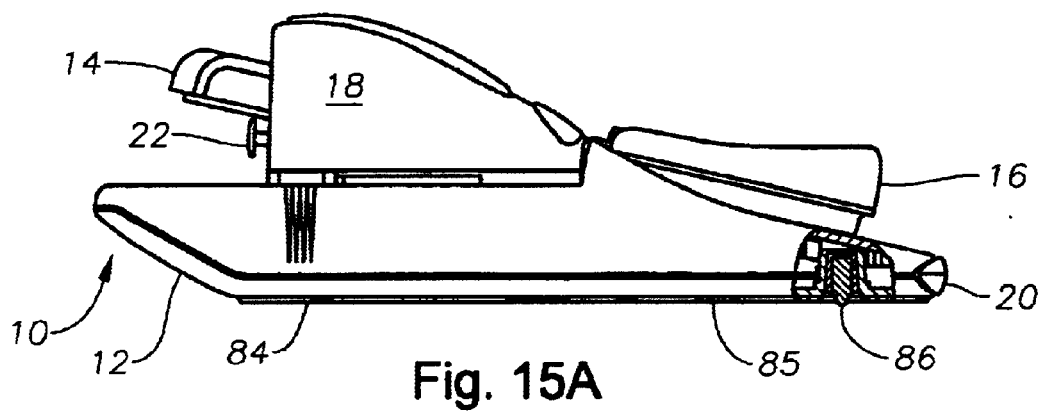
FIGS. 15A–15C are cross-sectional view of the footswitch of the present invention illustrating the operation of the anti-gravity spring plunger feet.
Figure 15B:
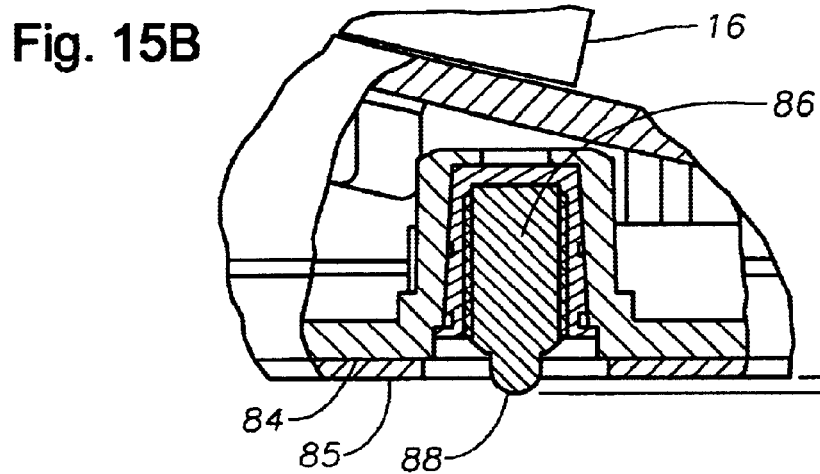
Figure 15C:
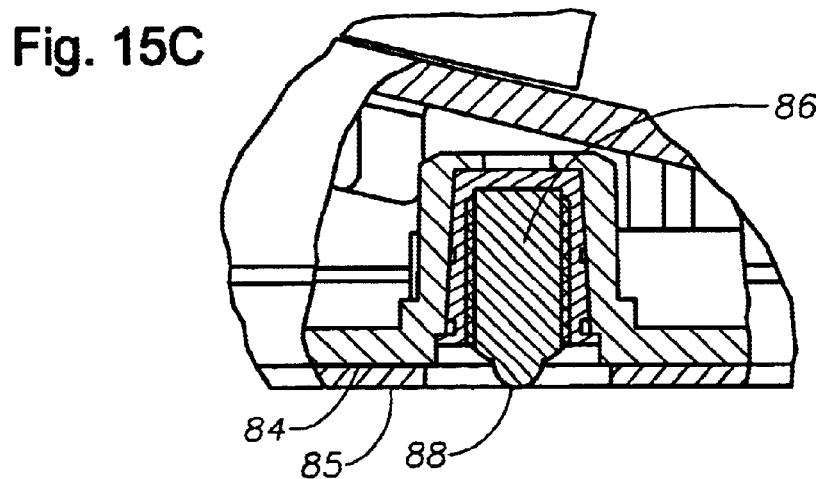

As shown in FIGS. 14 and 15A–15C, bottom 85 of base 12 preferably is covered by relatively high friction polymer (e.g., VERSAFLEX TPE) material 84 and contains a plurality of retractable, anti-gravity spring-loaded plunger feet 86 made from a low friction polymer material (e.g., DELRIN® acetal resin). As shown in FIGS. 15A and 15B, when there is no weight on footswitch 10, spring loaded plunger 86 project a short distance D (e.g., 0.04 inches) outwardly from bottom 84, thereby contacting the floor and allowing easy sliding of footswitch 10 on relatively low friction plunger tips 88. As shown in FIG. 15C, when weight is placed on footswitch 10, plungers 86 retract, and high friction bottom 84 contacts the floor, thereby making it more difficult to slide footswitch 10 during use.

This description is given for purposes of illustration and explanation. It will be apparent to those skilled in the relevant art that modifications may be made to the invention as herein described without departing from its scope or spirit.

We claim:

1. A surgical footswitch, comprising:
   a) a base;
   b) a treadle mounted to the base; and
   c) a pair of side switches rotationally mounted to the base on either side of the treadle, the switches being adjustable relative to the treadle so as to increase or decrease the distance between the switches.

2. The footswitch of claim 1 wherein the switches are locked in place by a locking pin fitted into the base being held within detents in the switches.

3. The footswitch of claim 1 wherein the position of the switches is visually indicated by switch position indicators.

4. The footswitch of claim 1 wherein the treadle contains a raised reference point for assisting in centering a foot on the treadle.

5. A surgical footswitch, comprising:
   a) a base;
   b) a treadle mounted to the base; and
   c) a heel cup rotationally mounted to the treadle so that the heel cup may be rotated along an axis perpendicular to the treadle and independently of any movement of the treadle.

6. The footswitch of claim 5 further comprising a pair of side switches rotationally mounted to the base on either side of the treadle, so that rotation of the heel cup allows operation of the switches independently of any movement of the treadle.

7. A surgical footswitch, comprising:
   a) a base having a bottom;
   b) a treadle pivotally and rotationally mounted to the base;
   c) a pair of side switches rotationally mounted to the base on either side of the treadle, the side switches being operable without movement of the treadle and adjustable relative to the treadle so as to increase or decrease the distance between the side switches;
   d) a heel cup slidable and rotatably retained on the treadle so as to adjustably increase or decrease a length of the treadle;
   e) a pair of switches mounted to the treadle so that rotation or counter-rotation of the treadle operates the switches;
   f) a plurality of plungers retractably mounted to the bottom; and
   g) a relatively high friction material mounted to the base bottom,
   wherein the plungers retract within the base when weight is placed on the footswitch and extend outwardly from the base and the relatively high friction material when no weight is placed on the footswitch.

8. The footswitch of claim 7 wherein the side switches are locked in place by a locking pin fitted into the base being held within detents in the side switches.

9. The footswitch of claim 7 wherein the position of the side switches is visually indicated by switch position indicators.

10. The footswitch of claim 7 wherein the treadle contains a raised reference point for assisting in centering a foot on the treadle.

11. The footswitch of claim 7 wherein the heel cup is prevented from sliding by a plurality of locking pins mounted on the heel cup, the locking pins fitting within locking holes in the treadle.

12. The footswitch of claim 7 wherein the position of the heel cup is visually indicated by position indicators.

* * * * *